(12) United States Patent
Shotey et al.

(10) Patent No.: US 8,084,718 B1
(45) Date of Patent: Dec. 27, 2011

(54) WAX MELTING SYSTEM

(75) Inventors: Marcus J. Shotey, Scottsdale, AZ (US); Jeffrey P. Baldwin, Phoenix, AZ (US)

(73) Assignee: TayMac Corporation, Gilbert, AZ (US)

( * ) Notice: Subject to any disclaimer, the term of this patent is extended or adjusted under 35 U.S.C. 154(b) by 1164 days.

(21) Appl. No.: 11/768,614

(22) Filed: Jun. 26, 2007

Related U.S. Application Data

(60) Provisional application No. 60/805,791, filed on Jun. 26, 2006.

(51) Int. Cl.
*A61F 7/00* (2006.01)
*A61F 7/08* (2006.01)
*F27B 14/14* (2006.01)
*F27B 14/18* (2006.01)

(52) U.S. Cl. ........ 219/428; 219/386; 219/422; 219/424; 219/432; 222/146.5

(58) Field of Classification Search .................. None
See application file for complete search history.

(56) References Cited

U.S. PATENT DOCUMENTS

| | | | | |
|---|---|---|---|---|
| 3,610,884 A | * | 10/1971 | Evans et al. | 219/439 |
| 4,696,303 A | * | 9/1987 | Bernardini | 607/104 |
| 4,880,415 A | * | 11/1989 | Urakami | 604/291 |
| 5,847,363 A | * | 12/1998 | Debourg et al. | 219/424 |
| 6,184,500 B1 | * | 2/2001 | Glucksman | 219/432 |
| 6,303,910 B2 | * | 10/2001 | Glucksman et al. | 219/430 |
| 6,417,495 B1 | * | 7/2002 | Glucksman | 219/432 |
| 6,573,481 B2 | * | 6/2003 | Glucksman | 219/432 |
| 6,627,072 B1 | * | 9/2003 | Ridge | 210/149 |
| 6,935,535 B2 | * | 8/2005 | Pandolfi et al. | 222/146.5 |
| 7,315,691 B1 | * | 1/2008 | Palkie et al. | 392/441 |
| 2001/0020613 A1 | * | 9/2001 | Glucksman et al. | 219/430 |
| 2007/0253687 A1 | * | 11/2007 | Palkie et al. | 392/441 |

* cited by examiner

*Primary Examiner* — Joseph M Pelham
(74) *Attorney, Agent, or Firm* — Booth Udall, PLC

(57) ABSTRACT

A wax melting system including a melting stage and a holding stage. Implementations may include a melting stage having a drain and the drain configured to permit flow of melted wax from the melting stage to the holding stage. A vessel may also be included. The melting stage and the holding stage may be coupled into the vessel and the melting stage oriented above the holding stage. The vessel may enclose the melting stage and the temperature of the melting stage may be maintained above the temperature of the holding stage.

18 Claims, 3 Drawing Sheets

WAX MELTING SYSTEM

CROSS REFERENCE TO RELATED APPLICATIONS

This document claims the benefit of the filing date of U.S. Provisional Patent Application 60/805,791, entitled "Wax Melting System" to Shotey, et al. which was filed on Jun. 26, 2006, the disclosure of which is hereby incorporated entirely herein by reference.

BACKGROUND

1. Technical Field

Aspects of this document relate generally to systems used for melting materials, such as wax.

2. Background Art

Conventional therapeutic wax melting systems consist of a single pan or vessel heated internally by electricity under thermostat control. Therapeutic wax melting using a conventional system has been accomplished by the user placing solid wax into the pan or vessel, turning on an internal heater, and waiting for the wax to melt to liquid form and then cool to the proper, therapeutic temperature. Once the wax is ready, the user inserts their hand, foot, elbow, etc. into the pan or vessel. After use, the internal heater is turned off, allowing the wax in the pan to solidify to await the next treatment.

SUMMARY

Implementations of a wax melting system may include a melting stage and a holding stage, the melting stage having a drain and the drain configured to permit flow of melted wax from the melting stage to the holding stage. A vessel may also be included. The melting stage and the holding stage may be coupled into the vessel and the melting stage oriented above the holding stage. The vessel may enclose the melting stage and the temperature of the melting stage may be maintained above the temperature of the holding stage.

Implementations of a wax melting system may include one, some or any of the following:

The vessel may include an electric power distribution system and the temperature of the melting stage may be maintained above the temperature of the holding stage through the electric power distribution system. The electric power distribution system may be coupled to the melting stage and the holding stage.

The holding stage may further include a drain and may include a drain closing mechanism.

Implementations of a therapeutic wax melter may include a melting tray and a holding tray, the melting tray and holding tray each having a valve, the valve of the melting tray oriented above the holding tray and configured to permit flow of melted wax out of the melting tray. A vessel configured to enclose the melting tray and the holding tray may be included and the melting tray and the holding tray may be coupled into the vessel. The vessel may include an electric power distribution system coupled to the melting tray and the holding tray. The temperature of the melting tray may be maintained above the temperature of the holding stage through the electric power distribution system.

Implementations of a wax melting system or therapeutic wax melter may include one, some, or any of the following:

The holding stage or tray and the melting stage or tray may be coupled to the vessel through a T-bracket coupled to the vessel.

A particular implementation of an electric power distribution system may include some, one, or all of the following:

A first set and a second set of electrical contacts may be included in the T-bracket, each set of electrical contacts having two contacts and the first set of electrical contacts oriented above the second set of electrical contacts. A first heating element and a second heating element may be included, the first heating element coupled to the first set of electrical contacts and the second heating element coupled to the second set of electrical contacts. The first heating element may be included in the melting stage or tray and the second heating element may be included in the holding stage or tray. The first heating element may be substantially identical to the second heating element. A transformer may also be included and the first set of electrical contacts may be maintained at a higher voltage than the second set of electrical contacts through the transformer.

Another particular implementation of an electric power distribution system may also include one, some, or all of the following:

A first set and a second set of electrical contacts may be included in the T-bracket, each set of electrical contacts having two contacts and the first set of electrical contacts oriented above the second set of electrical contacts. A first heating element and a second heating element may be included, the first heating element coupled to the first set of electrical contacts and the second heating element coupled to the second set of electrical contacts. The first heating element may be included in the melting stage or tray and the second heating element may be included in the holding stage or tray. The first heating element may be substantially identical to the second heating element. A melting stage or melting tray thermostat may be coupled to the first heating element and a holding stage or holding tray thermostat may be coupled to the second heating element. The first set of electrical contacts may be maintained at substantially the same voltage as the second set of electrical contacts, and the setpoint of the melting stage or melting tray thermostat may be higher than the setpoint of the holding stage or holding tray thermostat.

A third particular implementation of an electric power distribution system may include one, some, or all of the following:

A first set and a second set of electrical contacts may be included in the T-bracket, each set of electrical contacts having three contacts. The first set of electrical contacts may be oriented above the second set of electrical contacts. A first set of heating elements and a second set of heating elements may be included, the first set of heating elements selectively coupled to the first set of electrical contacts and the second set of heating elements selectively coupled to the second set of electrical contacts. The first set of heating elements may be included in the melting stage or tray and the second set of heating elements may be included in the holding stage or tray. The first set of heating elements may include a first heating element dissimilar from a second heating element. The second set of heating elements may include a first heating element substantially identical to the first heating element of the first set of heating elements and a second heating element substantially identical to the second heating element of the second set of heating elements. The first set of electrical contacts may be maintained at a substantially the same voltage as the second set of electrical contacts.

The melting stage or tray and holding stage or tray may be exchangeable within the vessel.

The melting stage or tray may engage a drain or valve opening mechanism when oriented above the holding stage or tray and the holding stage or tray may engage a drain or valve closing mechanism when oriented below the holding stage or tray.

The holding stage or tray may be integrally formed into the vessel.

Implementations of a wax melting system or therapeutic wax melter may utilize a method of melting therapeutic wax including the steps of orienting a melting stage above a holding stage, the melting stage having a valve configured to permit flow of melting wax out of the melting stage. The method may further include the steps of placing sold wax in the melting stage, maintaining the melting stage at a melting temperature of the wax, receiving melted wax from the melting stage into the holding stage, and maintaining the holding stage at a therapeutic wax temperature.

The method may further include the steps of removing the holding stage from the vessel and using the holding stage to apply therapeutic wax. The method may also include the step of exchanging the position of the holding stage and melting stage to remelt the wax.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The invention will hereinafter be described in conjunction with the appended drawings, where like designations denote like elements, and.

DESCRIPTION

This disclosure, its aspects and implementations, are not limited to the specific components or assembly procedures disclosed herein. Many additional components and assembly procedures known in the art consistent with the intended wax melting system and/or assembly procedures for a wax melting system will become apparent for use with particular implementations from this disclosure. Accordingly, for example, although particular implementations are disclosed, such implementations and implementing components may comprise any shape, size, style, type, model, version, measurement, concentration, material, quantity, and/or the like as is known in the art for such wax melting systems and implementing components, consistent with the intended operation.

Figure 1:
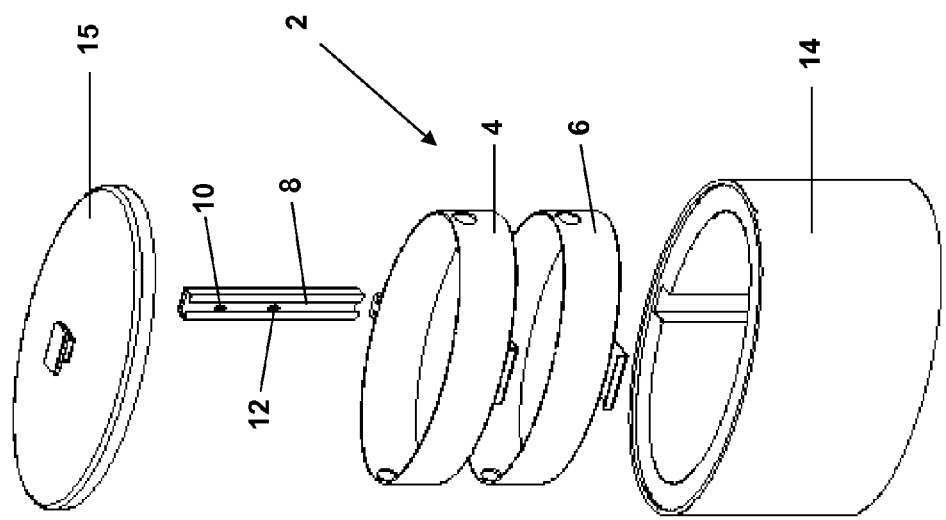
FIG. 1 is a front perspective exploded view of an implementation of a wax melting system.

Referring to FIG. 1, a particular implementation of a wax melting system 2 is illustrated. As shown by example in the illustration, implementations of a wax melting system 2 may include a melting stage 4 or melting tray 4 and a holding stage 6 or holding tray 6. The melting stage 4 and the holding stage 6 may each be coupled to a T-bracket 8 that may include at least two sets of electrical contacts 10, 12. The T-bracket 8 may be coupled to a vessel 14 which may be sized and shaped to fully enclose the melting stage 4 and holding stage 6 through a lid 15 or other enclosing feature while the wax melting system 2 is in use. An electrical power distribution system may be included as part of the vessel 14 and include the at least two sets of electrical contacts 10, 12. The electrical power distribution system may be coupled to the melting stage 4 and the holding stage 6 through the T-bracket 8. In particular implementations, the melting stage 4 and holding stage 6 may be oriented so that they overlap almost entirely as illustrated in FIG. 1. Other particular implementations may have the melting stage 4 and holding stage 6 overlapping only partially. In some implementations, the melting stage 4 and the holding stage 6 may not overlap at all. In all these latter implementations, however, the melting stage 4 may still be oriented vertically above the holding stage 6 to allow melting wax to flow from the melting stage 4 to the holding stage 6 during operation.

The at least two sets of electrical contacts 10, 12 may include a first set 10 and a second set 12. In a particular implementation of an electrical distribution system, the first set 10 and second set 12 of electrical contacts may each include two contacts. As illustrated in FIG. 1, the first set of electrical contacts 10 may be oriented vertically above the second set of electrical contacts 12 on the T-bracket 8. The first set of electrical contacts 10 may be in contact with a first heating element in the melting stage 4 and the second set of electrical contacts 12 may be in contact with a second heating element in the melting stage 4. The heating element may be integrally formed as part of the melting stage 4 or may be coupled to the melting stage 4. The first heating element may be substantially identical to the second heating element, meaning that the first and second heating element may be equivalent when compared in terms of, by non-limiting example, their watt output, resistance, and any other relevant parameters used in the art to determine the characteristics of a heating element. Relevant teachings regarding heating elements, their structure and materials may be found in U.S. Pat. No. 3,760,156 to Kehl et al., entitled "Detachable Electrical Heating Griddle" issued Sep. 18, 1973 and U.S. Pat. No. 3,678,844 to Marshall entitled "Food Cooking Grill" issued Jul. 25, 1972, the disclosures of which are hereby incorporated by reference. A transformer may be included as part of the electrical distribution system and may be used to maintain the first set of electrical contacts 10 at a higher voltage than the second set of electrical contacts 12, thereby increasing the heat output of the first heating element relative to the second, substantially identical, heating element and thus maintaining the temperature of the melting stage 4 above that of the holding stage 6.

In another particular implementation of an electric power distribution system, the first set of electrical contacts 10 and second set of electrical contacts 12 may be maintained at substantially the same voltage and each coupled to a first heating element in the melting stage 4 and in the holding stage 6, respectively. The electrical power distribution system may further include a melting stage thermostat and a holding stage thermostat. The setpoint on the melting stage thermostat may be set higher than the setpoint of the holding stage thermostat, thereby maintaining the melting stage 4 at a higher temperature by applying electric power to the first heating element more frequently than the holding stage thermostat. Relevant teachings regarding the structure and materials of thermostats may be found in U.S. Pat. No. 4,605,841 to Fischer et al. entitled "Thermostat for Electric Hotplate," the disclosure of which is hereby incorporated herein by reference.

In a third particular implementation of an electrical power distribution system, both the first and second sets of electrical contacts 10, 12 may each include three contacts. The melting stage 4 and holding stage 6 may each include a first set and a second set of heating elements. The first set of heating elements may be dissimilar from the second with respect to, by non-limiting example, wattage, resistance, and any other any other relevant parameters used in the art to determine the characteristics of a heating element. Both the melting stage 4 and the holding stage 6 may include first sets and second sets of heating elements that are substantially identical. The first set of electrical contacts 10 may be selectively coupled to the first set of heating elements in the melting stage 4 by structurally arranging the set of three contacts to correspond to the input(s) to the first set of heating elements. The second set of electrical contacts 12 may be selectively coupled to the second set of heating elements in the holding stage 6 by structurally arranging the set of three contacts to correspond to the input(s) to the second set of heating elements. In other particular implementations, the first set of electrical contacts 10 may be selectively coupled to the second set of heating elements in the melting stage 4 and the second set of electrical contacts 12 may be selectively coupled to the first set of heating elements in the holding stage 6. The first set of electrical contacts may be maintained at substantially the same voltage as the second set of electrical contacts, thus enabling the melting stage 4 to operate at a temperature above that of the holding stage 6 through the difference in output power between the first set and second set of heating elements.

Figure 2B:
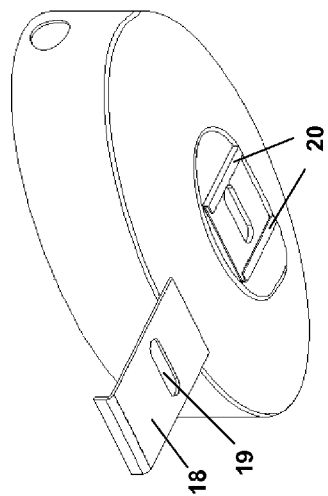
FIG. 2B is a bottom perspective exploded view of a tray.
Figure 2A:
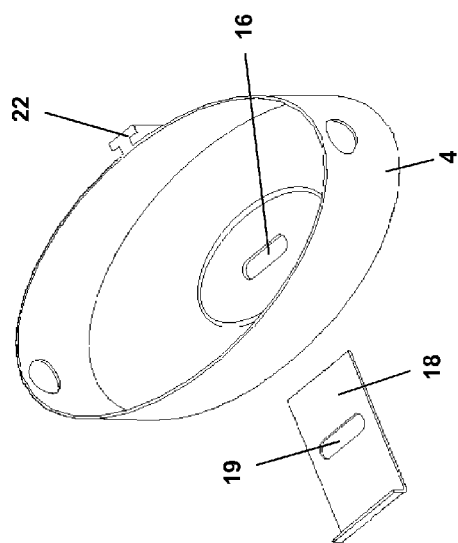
FIG. 2A is a top perspective exploded view of a tray.

Referring to FIG. 2A, a particular implementation of a melting stage 4 is illustrated. As illustrated, particular implementations of a melting stage 4 may take the form of a tray and may include a drain 16. The positioning of the drain 16 in the tray is not crucial, but particular implementations of the wax melting system comprise a bottom tray wall that is sloped toward the drain 16. In particular implementations of a wax melting system 2, the melting stage 4 and holding stage 6 may both be trays and may also be exchangeable; that is, they may each be coupled to either the first set of electrical contacts 10 or the second set of electrical contacts 12 of the T-bracket 8. In other particular implementations, the holding stage 6 may be integrally formed with the vessel 14. The drain 16 may include a valve 18, which, in particular implementations, may take the form of a sliding plate with an orifice 19 therethrough as illustrated in FIG. 2A. Referring to FIG. 2B, the valve 18 may be coupled to the melting stage 4 through rails 20. The valve 18 may be spring loaded to bias it to an open position. The valve may be in the open position when the orifice 19 is aligned with the drain 16, allowing melted wax to flow from the melting stage 4 into the holding stage 6. Particular implementations of a wax melting system 2 may utilize a wide variety of valves 18, including, by non-limiting example, check valves, electronically actuated valves, manually operated valves, solenoid valves, and any other type of mechanism capable of closing or opening the drain 16 of the melting stage 4 manually and/or automatically. The melting stage 4 may also include a T-shaped fitting 22 shaped to engage with the T-bracket 8 and which, in particular implementations, may also engage with the first and second sets of electrical contacts 10, 12 and thereby transmit electrical power to the heating elements in the melting stage 4.

Figure 3:
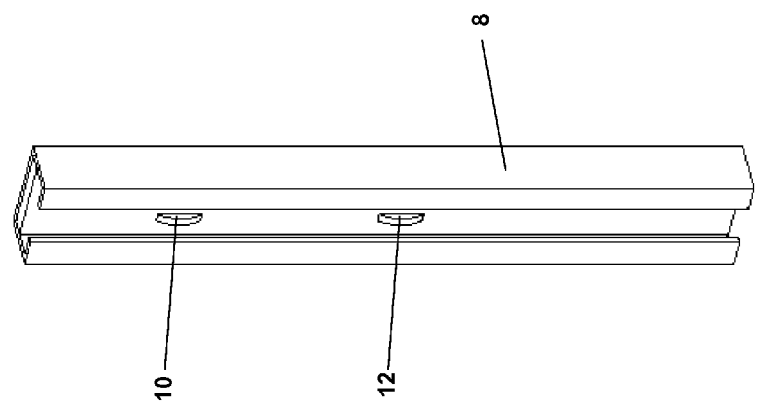
FIG. 3 is a perspective view of a T-bracket.

Referring to FIG. 3, a particular implementation of a T-bracket 8 showing the first set of electrical contacts 10 and the second set of electrical contacts 12 are illustrated. Electrical contacts may also be implemented through the side rails of the T-bracket 8. The T-bracket 8 may slidably couple into the vessel 14 and may also include at least one electrical connector to couple with the electrical power distribution system. Use of a T-bracket 8 may help prevent users of a wax melting system 2 from contacting the first and second sets of electrical connectors 10, 12 while operating the system. In particular implementations where the melting stage 6 and the holding stage 8 are exchangeable, the vessel 14 or the T-bracket 8 may include a drain or valve closing mechanism to close the valve 18 of the holding stage 6 while it is coupled into the vessel 8. The valve 18 of the melting stage 4 may be kept open to allow melted wax to flow from the melting stage 4 to the holding stage 6.

Implementations of a wax melting system 2, assemblies, and implementing components, may be constructed of a wide variety of materials. For example, the components may be formed of: rubbers (synthetic and/or natural) and/or other like materials; glasses (such as fiberglass), carbon-fiber, aramid-fiber, any combination thereof, and/or other like materials; polymers such as thermoplastics (such as ABS, Fluoropolymers, Polyacetal, Polyamide; Polycarbonate, Polyethylene, Polysulfone, and/or the like), thermosets (such as Epoxy, Phenolic Resin, Polyimide, Polyurethane, Silicone, and/or the like), any combination thereof, and/or other like materials; composites and/or other like materials; metals, such as zinc, magnesium, titanium, copper, lead, iron, steel, carbon steel, alloy steel, tool steel, stainless steel, brass, tin, antimony, aluminum, any combination thereof, and/or other like materials; alloys, such as aluminum alloy, titanium alloy, magnesium alloy, copper alloy, any combination thereof, and/or other like materials; any other suitable material, such as a refractory material; and/or any combination of the foregoing thereof. For the exemplary purposes of this disclosure, the melting and holding stages 4, 6, and the T-bracket 8 may be formed of a metal, such as aluminum. The melting and holding stages 4, 6, may also be coated with a material that may reduce sticking or burning of the wax material. This coating may be constructed of one of the foregoing listed materials, and for the exemplary purposes of this disclosure, the coating material may be a Teflon® fluoropolymer.

Some components defining wax melting system implementations may be manufactured simultaneously and integrally joined with one another, while other components may be purchased pre-manufactured or manufactured separately and then assembled with the integral components. Various implementations may be manufactured using conventional procedures as added to and improved upon through the procedures described here.

Accordingly, manufacture of these components separately or simultaneously may involve vacuum forming, injection molding, blow molding, casting, forging, cold rolling, milling, drilling, reaming, turning, grinding, stamping, pressing, cutting, bending, welding, soldering, hardening, riveting, punching, plating, and/or the like. Components manufactured separately may then be coupled or removably coupled with the other integral components in any manner, such as with adhesive, a weld joint, a solder joint, a fastener (e.g. a bolt and a nut, a screw, a rivet, a pin, and/or the like), washers, retainers, wrapping, wiring, any combination thereof, and/or the like for example, depending on, among other considerations, the particular material forming the components. For the exemplary purposes of this disclosure, the melting and holding stage 4, 6 may be press formed, then anodized.

Implementations of a wax melting system 2 may be utilized to provide therapeutic wax for use in treating various body parts. Therapeutic wax typically is obtained in solid form and must first be melted to and maintained at a comfortable therapeutic temperature prior to application to the user's foot or hand. Accordingly, solid wax may be placed in the melting stage 4 and the vessel 14 connected to an electric power source. The electric power distribution system may heat the melting stage 4 to a temperature sufficient to melt the wax, and may maintain the melting stage 4 significantly above the actual wax melting temperature but below its flashpoint (248 F, for paraffin wax, for example) for safety reasons. As the wax melts, the liquid wax may run out through the drain 16 through the open valve 18 into the holding stage 6, which is maintained through the electric power distribution system at the therapeutic temperature at which the wax can be comfortably used. The therapeutic temperature is high enough to keep the wax liquid, but low enough to avoid discomfort to the user. Therapeutic wax temperatures are known in the art and may vary by the tolerance of the user. Because the melted wax may rapidly flow from the melting stage 4 to the holding stage 6, it may not appreciably rise in temperature above the melting point of the wax after melting. Accordingly, the melting stage 4 may be operated at a temperature significantly above the melting point of the wax, enabling the wax to melt rapidly while not significantly further heating the liquid wax being produced. This feature of the wax melting system 2 reduces or eliminates the need for a user to wait after the wax is melted to use the wax. Once the desired quantity of melted wax is contained in the holding stage 6, in particular implementations of a wax melting system 2, the holding stage 6 may be removed from the vessel 14 and the user may utilize the holding stage 6 to apply the wax. In other implementations, the melted wax may be poured from the holding stage 6 into another suitable container for use. In implementations where the melting stage 4 and holding stage 6 are exchangeable, after the user has finished applying the wax, the cooled wax in the holding tray may be remelted by reversing the positions of the holding stage 6 and melting stage 4 in the vessel and applying electrical power through the electric power distribution system. In these implementations, the wax may be ready for reuse in a relatively short period of time.

It will be understood that implementations are not limited to the specific components disclosed herein, as virtually any components consistent with the intended operation of a method and/or system implementation for a wax melting system may be utilized. Accordingly, for example, although particular trays, T-brackets and vessels may be disclosed, such components may comprise any shape, size, style, type, model, version, class, grade, measurement, concentration, material, weight, quantity, and/or the like consistent with the intended operation of a method and/or system implementation for a was melting system may be used.

In places where the description above refers to particular implementations of a wax melting system, it should be readily apparent that a number of modifications may be made without departing from the spirit thereof and that these implementations may be applied to other wax melting systems. The accompanying claims are intended to cover such modifications as would fall within the true spirit and scope of the disclosure set forth in this document. The presently disclosed implementations are, therefore, to be considered in all respects as illustrative and not restrictive, the scope of the disclosure being indicated by the appended claims rather than the foregoing description. All changes that come within the meaning of and range of equivalency of the claims are intended to be embraced therein.

The invention claimed is:

1. A wax melting system comprising:
   a melting stage and a holding stage, the melting stage comprising a drain, the drain configured to permit flow of melted wax from the melting stage to the holding stage; and
   a vessel;
   wherein the melting stage and the holding stage are coupled into the vessel, the melting stage is oriented above the holding stage and slidably mounted to a bracket coupled to the vessel to permit the melting stage to be raised and lowered in relation to the holding stage while the melting stage is slidably mounted to the bracket, and the vessel encloses both the holding stage and the melting stage during a heating operation; and
   wherein the temperature of the melting stage is maintained above the temperature of the holding stage.

2. The wax melting system of claim 1, wherein the vessel comprises an electric power distribution system and the temperature of the melting stage is maintained above the temperature of the holding stage through the electric power distribution system.

3. The wax melting system of claim 2, wherein the electric power distribution system is coupled to the melting stage and the holding stage through the bracket coupled to the vessel.

4. The wax melting system of claim 3, wherein the electric power distribution system further comprises:
   a first set and a second set of electrical contacts comprised in the bracket, each set of electrical contacts comprising two contacts, the first set of electrical contacts oriented above the second set of electrical contacts;
   a first heating element and a second heating element, the first heating element coupled to the first set of electrical contacts and the second heating element coupled to the second set of electrical contacts, the first heating element comprised in the melting stage and the second heating element comprised in the holding stage, the first heating element substantially identical to the second heating element; and
   a transformer;
   wherein the first set of electrical contacts is maintained at a higher voltage than the second set of electrical contacts through the transformer.

5. The wax melting system of claim 3, wherein the electric power distribution system further comprises:
   a first set and a second set of electrical contacts comprised in the bracket, each set of electrical contacts comprising two contacts, the first set of electrical contacts oriented above the second set of electrical contacts;
   a first heating element and a second heating element, the first heating element coupled to the first set of electrical contacts and the second heating element coupled to the second set of electrical contacts, the first heating element comprised in the melting stage and the second heating element comprised in the holding stage, the first heating element substantially identical to the second heating element; and
   a melting stage thermostat coupled to the first heating element and a holding stage thermostat coupled to the second heating element;
   wherein the first set of electrical contacts is maintained at substantially the same voltage as the second set of electrical contacts, and the setpoint of the melting stage thermostat is higher than the setpoint of the holding stage thermostat.

6. The wax melting system of claim 3, wherein the electric power distribution system further comprises:
   a first set of electrical contacts and a second set of electrical contacts comprised in the bracket, each set of electrical contacts comprising three contacts, the first set of electrical contacts oriented above the second set of electrical contacts; and
   a first set of heating elements and a second set of heating elements, the first set of heating elements selectively coupled to the first set of electrical contacts and the second set of heating elements selectively coupled to the second set of electrical contacts, the first set of heating elements comprised in the holding stage, the first set of heating elements comprising a first heating element dissimilar from a second heating element and the second set of heating elements comprising a first heating element substantially identical to the first heating element of the first set of heating elements and a second heating element substantially identical to the second heating element of the first set of heating elements;

wherein the first set of electrical contacts is maintained at a substantially the same voltage as the second set of electrical contacts.

7. The wax melting system of claim 1, wherein the melting stage and holding stage are exchangeable within the vessel.

8. The wax melting system of claim 7, wherein the melting stage engages a drain opening mechanism when oriented above the holding stage and the holding stage further comprises a drain and engages a drain closing mechanism when oriented below the holding stage.

9. The wax melting system of claim 1, wherein the holding stage is integrally formed as part of the vessel.

10. A therapeutic wax melter comprising:
    a melting tray and a holding tray, the melting tray and holding tray each comprising a valve, the valve of the melting tray oriented above the holding tray and configured to permit flow of melted wax out of the melting tray; and
    a vessel configured to enclose the melting tray and the holding tray, the melting tray and holding tray coupled into the vessel;
    wherein the vessel comprises an electric power distribution system coupled to the melting tray and the holding tray; and
    wherein the temperature of the melting tray is maintained above the temperature of the holding stage through the electric power distribution system.

11. The wax melting system of claim 10, wherein the wax melting tray and holding tray are coupled to the vessel through a bracket coupled to the vessel.

12. The wax melting system of claim 11, wherein the electric power distribution system further comprises:
    a first set and a second set of electrical contacts comprised in the bracket, each set of electrical contacts comprising two contacts, the first set of electrical contacts oriented above the second set of electrical contacts;
    a first heating element and a second heating element, the first heating element coupled to the first set of electrical contacts and the second heating element coupled to the second set of electrical contacts, the first heating element comprised in the melting tray and the second heating element comprised in the holding tray, the first heating element substantially identical to the second heating element; and
    a transformer;
    wherein the first set of electrical contacts is maintained at a higher voltage than the second set of electrical contacts through the transformer.

13. The wax melting system of claim 11, wherein the electric power distribution system further comprises:
    a first set and a second set of electrical contacts comprised in the bracket, each set of electrical contacts comprising two contacts, the first set of electrical contacts oriented above the second set of electrical contacts;
    a first heating element and a second heating element, the first heating element coupled to the first set of electrical contacts and the second heating element coupled to the second set of electrical contacts, the first heating element comprised in the melting tray and the second heating element comprised in the holding tray, the first heating element substantially identical to the second heating element; and
    a melting stage thermostat coupled to the first heating element and a holding stage thermostat coupled to the second heating element;
    wherein the first set of electrical contacts is maintained at substantially the same voltage as the second set of electrical contacts, and the setpoint of the melting stage thermostat is higher than the setpoint of the holding stage thermostat.

14. The wax melting system of claim 11, wherein the electrical power distribution system further comprises:
    a first set and a second set of electrical contacts comprised in the bracket, each set of electrical contacts comprising three contacts, the first set of electrical contacts oriented above the second set; and
    a first set of heating elements and a second set of heating elements, the first set of heating elements selectively coupled to the first set of electrical contacts and the second set of heating elements selectively coupled to the second set of electrical contacts, the first set of heating elements comprised in the melting tray and the second set of heating elements comprised in the holding tray, the first set of heating elements comprising a first heating element dissimilar from a second heating element and the second set of heating elements comprising a first heating element substantially identical to the first heating element of the first set of heating elements and a second heating element substantially identical to the second heating element of the first set of heating elements;
    wherein the first set of electrical contacts is maintained at a substantially higher voltage than the second set of electrical contacts.

15. The wax melting system of claim 10, wherein the melting tray and the holding tray are exchangeable within the vessel.

16. The wax melting system of claim 15, wherein the melting tray engages a valve opening mechanism when oriented above the holding tray and the holding tray engages a valve closing mechanism when oriented below the holding tray.

17. The wax melting system of claim 10, wherein the holding tray is integrally formed into the vessel.

18. A method of melting therapeutic wax, the method comprising:
    orienting a melting stage above a holding stage, the melting stage comprising a valve configured to permit flow of melting wax out of the melting stage;
    placing solid wax in the melting stage;
    maintaining the melting stage at a melting temperature of the wax;
    receiving melted wax from the melting stage into the holding stage;
    maintaining the holding stage at a therapeutic wax temperature; and
    exchanging the position of the holding stage and the melting stage to remelt the wax.

* * * * *